US009183647B2

(12) United States Patent
Morton (10) Patent No.: US 9,183,647 B2
(45) Date of Patent: *Nov. 10, 2015

(54) IMAGING, DATA ACQUISITION, DATA TRANSMISSION, AND DATA DISTRIBUTION METHODS AND SYSTEMS FOR HIGH DATA RATE TOMOGRAPHIC X-RAY SCANNERS

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/312,540

(22) Filed: Jun. 23, 2014

(65) Prior Publication Data

US 2015/0071399 A1    Mar. 12, 2015

Related U.S. Application Data

(63) Continuation of application No. 12/787,878, filed on May 26, 2010, now Pat. No. 8,804,899, which is a continuation-in-part of application No. 12/485,897, filed on Jun. 16, 2009, now abandoned, which is a (Continued)

(51) Int. Cl.
*A61B 6/00* (2006.01)
*G06T 11/00* (2006.01)
(Continued)

(52) U.S. Cl.
CPC ............... *G06T 11/005* (2013.01); *A61B 6/032* (2013.01); *A61B 6/4085* (2013.01); *A61B 6/463* (2013.01); *A61B 6/542* (2013.01); *G01N 23/046* (2013.01); *G01T 1/17* (2013.01); *G01T 1/2985* (2013.01);
(Continued)

(58) Field of Classification Search
CPC ........ A61B 6/032; A61B 6/463; A61B 6/542; A61B 6/4028; A61B 6/4085; G01N 23/046
See application file for complete search history.

(56) References Cited

U.S. PATENT DOCUMENTS 3,768,645 A  10/1973  Conway
4,105,922 A   8/1978  Lambert
(Continued)

FOREIGN PATENT DOCUMENTS

DE   2729353 A1   1/1979
EP   0432568      6/1991
(Continued)

OTHER PUBLICATIONS

US 5,987,079, 11/1999, Scott (withdrawn).
(Continued)

*Primary Examiner* — Courtney Thomas
(74) *Attorney, Agent, or Firm* — Novel IP (57) ABSTRACT

The present invention is an X-ray system having a source-detector module, which includes X-ray sources and detectors, for scanning an object being inspected, a scan engine coupled to the source-detector module for collecting scan data from the source detector module, an image reconstruction engine coupled to the scan engine for converting the collected scan data into one or more X-ray images, and a scan controller coupled with at least one of the source detector module, the scan engine, and the image reconstruction engine optimize operations of the X-ray system.

20 Claims, 7 Drawing Sheets

Related U.S. Application Data continuation of application No. 10/554,656, which is a continuation of application No. PCT/GB2004/001729, filed on Apr. 23, 2004, now Pat. No. 7,564,939, said application No. 12/787,878 is a continuation-in-part of application No. 12/371,853, filed on Feb. 16, 2009, now Pat. No. 7,903,789, which is a continuation of application No. 10/554,975, which is a continuation of application No. PCT/GB2004/001741, filed on Apr. 23, 2004, now Pat. No. 7,512,215, said application No. 12/787,878 is a continuation-in-part of application No. 12/651,479, filed on Jan. 3, 2010, now abandoned, which is a continuation of application No. 10/554,654, filed on Feb. 7, 2008, which is a continuation of application No. PCT/GB2004/001731, filed on Apr. 23, 2004, now Pat. No. 7,664,230, said application No. 12/787,878 is a continuation-in-part of application No. 12/364,067, filed on Feb. 2, 2009, now abandoned, which is a continuation of application No. 12/033,035, filed on Feb. 19, 2008, now Pat. No. 7,505,563, which is a continuation of application No. 10/554,569, which is a continuation of application No. PCT/GB04/01732, filed on Apr. 25, 2003, now Pat. No. 7,349,525, said application No. 12/787,878 is a continuation-in-part of application No. 12/758,764, filed on Apr. 12, 2010, now Pat. No. 7,929,663, which is a continuation of application No. 12/211,219, filed on Sep. 16, 2008, now Pat. No. 7,724,868, which is a continuation of application No. 10/554,655, which is a continuation of application No. PCT/GB2004/001751, filed on Apr. 23, 2004, now Pat. No. 7,440,543, said application No. 12/787,878 is a continuation-in-part of application No. 12/697,073, filed on Jan. 29, 2010, now Pat. No. 8,085,897, which is a continuation of application No. 10/554,570, which is a continuation of application No. PCT/GB2004/001747, filed on Apr. 23, 2004, now Pat. No. 7,684,538, said application No. 12/787,878 is a continuation-in-part of application No. 12/142,005, filed on Jun. 19, 2008, now Pat. No. 8,135,110, which is a continuation of application No. 12/097,422, which is a continuation of application No. PCT/GB2006/004684, filed on Dec. 15, 2006, now Pat. No. 7,876,879, said application No. 12/787,878 is a continuation-in-part of application No. 12/478,757, filed on Jun. 4, 2009, now Pat. No. 8,094,784, which is a continuation of application No. 12/364,067, filed on Feb. 2, 2009, now abandoned, said application No. 12/787,878 is a continuation of application No. 12/712,476, filed on Feb. 25, 2010, now Pat. No. 8,243,876.

(60) Provisional application No. 61/155,572, filed on Feb. 26, 2009, provisional application No. 61/181,077, filed on May 26, 2009.

(51) Int. Cl.
    *A61B 6/03*     (2006.01)
    *G01T 1/29*     (2006.01)
    *G01N 23/04*     (2006.01)
    *G01T 1/17*     (2006.01)

(52) U.S. Cl.
    CPC ......... *A61B 6/4028* (2013.01); *G01N 2223/419* (2013.01); *G01N 2223/612* (2013.01)

(56) References Cited

U.S. PATENT DOCUMENTS

| | | | |
|---|---|---|---|
| 4,228,353 | A | 10/1980 | Johnson |
| 4,259,721 | A | 3/1981 | Kuznia |
| 4,266,425 | A | 5/1981 | Allport |
| 4,352,021 | A | 9/1982 | Boyd |
| 4,868,856 | A | 9/1989 | Frith |
| 4,987,584 | A | 1/1991 | Doenges |
| 5,033,106 | A | 7/1991 | Kita |
| 5,182,764 | A | 1/1993 | Peschmann |
| 5,257,183 | A | 10/1993 | Tam |
| 5,272,627 | A | 12/1993 | Maschhoff |
| 5,313,511 | A | 5/1994 | Annis |
| 5,319,547 | A | 6/1994 | Krug |
| 5,319,693 | A | 6/1994 | Eberhard |
| 5,367,552 | A | 11/1994 | Peschmann |
| 5,410,156 | A | 4/1995 | Miller |
| 5,461,650 | A | 10/1995 | Tam |
| 5,467,377 | A | 11/1995 | Dawson |
| 5,490,196 | A | 2/1996 | Rudich |
| 5,490,218 | A | 2/1996 | Krug |
| 5,557,108 | A | 9/1996 | Tumer |
| 5,600,303 | A | 2/1997 | Husseiny |
| 5,600,700 | A | 2/1997 | Krug |
| 5,606,167 | A | 2/1997 | Miller |
| 5,642,393 | A | 6/1997 | Krug |
| 5,661,774 | A | 8/1997 | Gordon |
| 5,712,926 | A | 1/1998 | Eberhard |
| 5,796,802 | A | 8/1998 | Gordon |
| 5,818,897 | A | 10/1998 | Gordon |
| 5,838,758 | A | 11/1998 | Krug |
| 5,859,891 | A | 1/1999 | Hibbard |
| 5,881,122 | A | 3/1999 | Crawford |
| 5,887,047 | A | 3/1999 | Bailey |
| 5,901,198 | A | 5/1999 | Crawford |
| 5,905,806 | A | 5/1999 | Eberhard |
| 5,909,477 | A | 6/1999 | Crawford |
| 5,910,973 | A | 6/1999 | Grodzins |
| 5,930,326 | A | 7/1999 | Rothschild |
| 5,974,111 | A | 10/1999 | Krug |
| 5,982,843 | A | 11/1999 | Bailey |
| 6,018,562 | A | 1/2000 | Willson |
| 6,021,174 | A | 2/2000 | Campbell |
| 6,026,143 | A | 2/2000 | Simanovsky |
| 6,026,171 | A | 2/2000 | Hiraoglu |
| 6,035,014 | A | 3/2000 | Hiraoglu |
| 6,037,597 | A | 3/2000 | Karavolos |
| 6,067,366 | A | 5/2000 | Simanovsky |
| 6,075,871 | A | 6/2000 | Simanovsky |
| 6,076,400 | A | 6/2000 | Bechwati |
| 6,078,642 | A | 6/2000 | Simanovsky |
| 6,088,423 | A | 7/2000 | Krug |
| 6,091,795 | A | 7/2000 | Schafer |
| 6,108,396 | A | 8/2000 | Bechwati |
| 6,111,974 | A | 8/2000 | Hiraoglu |
| 6,118,852 | A | 9/2000 | Rogers |
| 6,122,343 | A | 9/2000 | Pidcock |
| 6,128,365 | A | 10/2000 | Bechwati |
| 6,163,591 | A | 12/2000 | Benjamin |
| 6,181,765 | B1 | 1/2001 | Sribar |
| 6,183,139 | B1 | 2/2001 | Solomon |
| 6,185,272 | B1 | 2/2001 | Hiraoglu |
| 6,188,745 | B1 | 2/2001 | Gordon |
| 6,195,444 | B1 | 2/2001 | Simanovsky |
| 6,216,540 | B1 | 4/2001 | Nelson |
| 6,218,943 | B1 | 4/2001 | Ellenbogen |
| 6,236,709 | B1 | 5/2001 | Perry |
| 6,240,157 | B1 | 5/2001 | Danielsson |
| 6,252,929 | B1 | 6/2001 | Swift |
| 6,256,404 | B1 | 7/2001 | Gordon |
| 6,269,142 | B1 | 7/2001 | Smith |
| 6,272,230 | B1 | 8/2001 | Hiraoglu |
| 6,292,533 | B1 | 9/2001 | Swift |
| 6,304,629 | B1 | 10/2001 | Conway |
| 6,317,509 | B1 | 11/2001 | Simanovsky |
| 6,324,243 | B1 | 11/2001 | Edic |
| 6,324,249 | B1 | 11/2001 | Fazzio |

(56) References Cited

U.S. PATENT DOCUMENTS

| | | |
|---|---|---|
| 6,345,113 B1 | 2/2002 | Crawford |
| 6,373,916 B1 | 4/2002 | Inoue |
| 6,408,044 B2 | 6/2002 | Sembritzki |
| 6,411,670 B1 | 6/2002 | Besson |
| 6,417,797 B1 | 7/2002 | Cousins |
| 6,418,189 B1 | 7/2002 | Schafer |
| 6,429,578 B1 | 8/2002 | Danielsson |
| 6,430,255 B2 | 8/2002 | Fenkart |
| 6,445,765 B1 | 9/2002 | Frank |
| 6,459,755 B1 | 10/2002 | Li |
| 6,459,761 B1 | 10/2002 | Grodzins |
| 6,459,764 B1 | 10/2002 | Chalmers |
| 6,546,072 B1 | 4/2003 | Chalmers |
| 6,556,653 B2 | 4/2003 | Hussein |
| 6,563,906 B2 | 5/2003 | Hussein |
| 6,590,956 B2 | 7/2003 | Fenkart |
| 6,618,466 B1 | 9/2003 | Ning |
| 6,647,091 B2 | 11/2003 | Fenkart |
| 6,647,094 B2 | 11/2003 | Harding |
| 6,647,095 B2 | 11/2003 | Hsieh |
| 6,687,333 B2 | 2/2004 | Carroll |
| 6,707,879 B2 | 3/2004 | McClelland |
| 6,721,387 B1 | 4/2004 | Naidu |
| 6,735,271 B1 | 5/2004 | Rand |
| 6,737,652 B2 | 5/2004 | Lanza |
| 6,748,043 B1 | 6/2004 | Dobbs |
| 6,760,407 B2 | 7/2004 | Price |
| 6,770,884 B2 | 8/2004 | Bryman |
| 6,778,629 B1 | 8/2004 | Danielsson |
| 6,788,761 B2 | 9/2004 | Bijjani |
| 6,816,571 B2 | 11/2004 | Karimi |
| 6,827,265 B2 | 12/2004 | Bijjani |
| 6,830,185 B2 | 12/2004 | Knowles |
| 6,837,432 B2 | 1/2005 | Tsikos |
| 6,856,667 B2 | 2/2005 | Tsikos |
| 6,859,512 B2 | 2/2005 | Bruder |
| 6,859,514 B2 | 2/2005 | Hoffman |
| 6,901,135 B2 | 5/2005 | Fox |
| 6,906,329 B2 | 6/2005 | Bryman |
| 6,907,101 B2 | 6/2005 | Hoffman |
| 6,922,460 B2 | 7/2005 | Skatter et al. |
| 6,922,461 B2 | 7/2005 | Kang |
| 6,934,354 B2 | 8/2005 | Hoffman |
| 6,944,264 B2 | 9/2005 | Bijjani |
| 6,950,492 B2 | 9/2005 | Besson |
| 6,950,493 B2 | 9/2005 | Besson |
| 6,952,153 B2 | 10/2005 | Huey |
| 6,953,935 B1 | 10/2005 | Hoffman |
| 6,962,289 B2 | 11/2005 | Vatan |
| 6,968,034 B2 | 11/2005 | Hoffman |
| 6,971,577 B2 | 12/2005 | Ellenbogen |
| 6,973,158 B2 | 12/2005 | Besson |
| 6,975,698 B2 | 12/2005 | Katcha et al. |
| 6,978,936 B2 | 12/2005 | Wilson |
| 6,980,627 B2 | 12/2005 | Qiu |
| 6,990,171 B2 | 1/2006 | Toth |
| 6,990,172 B2 | 1/2006 | Toth |
| 6,993,115 B2 | 1/2006 | McGuire |
| 6,996,209 B2 | 2/2006 | Marek |
| 7,010,083 B2 | 3/2006 | Hoffman |
| 7,016,459 B2 | 3/2006 | Ellenbogen |
| 7,020,242 B2 | 3/2006 | Beneke |
| 7,023,957 B2 | 4/2006 | Bijjani |
| 7,027,553 B2 | 4/2006 | Dunham |
| 7,027,554 B2 | 4/2006 | Gaultier |
| 7,031,434 B1 | 4/2006 | Saunders |
| 7,034,313 B2 | 4/2006 | Hoffman |
| 7,039,154 B1 | 5/2006 | Ellenbogen |
| 7,046,756 B2 | 5/2006 | Hoffman |
| 7,046,761 B2 | 5/2006 | Ellenbogen |
| 7,054,408 B2 | 5/2006 | Jiang |
| 7,062,009 B2 | 6/2006 | Karimi |
| 7,062,074 B1 | 6/2006 | Beneke |
| 7,064,334 B2 | 6/2006 | Hoffman |
| 7,065,179 B2 | 6/2006 | Block |
| 7,068,750 B2 | 6/2006 | Toth |
| 7,068,751 B2 | 6/2006 | Toth |
| 7,072,434 B1 | 7/2006 | Tybinkowski |
| 7,076,029 B2 | 7/2006 | Toth |
| 7,078,699 B2 | 7/2006 | Seppi |
| 7,081,628 B2 | 7/2006 | Granfors |
| 7,084,404 B2 | 8/2006 | Hoffman |
| 7,088,799 B2 | 8/2006 | Hoffman |
| 7,090,133 B2 | 8/2006 | Hoffman |
| 7,092,481 B2 | 8/2006 | Hoffman |
| 7,092,485 B2 | 8/2006 | Kravis |
| 7,103,137 B2 | 9/2006 | Seppi |
| 7,110,488 B2 | 9/2006 | Katcha |
| 7,112,797 B2 | 9/2006 | Hoge |
| 7,116,749 B2 | 10/2006 | Besson |
| 7,116,751 B2 | 10/2006 | Ellenbogen |
| 7,119,553 B2 | 10/2006 | Yang |
| 7,123,681 B2 | 10/2006 | Ellenbogen |
| 7,127,027 B2 | 10/2006 | Hoffman |
| 7,130,374 B1 | 10/2006 | Jacobs |
| 7,133,491 B2 | 11/2006 | Bernardi |
| 7,136,450 B2 | 11/2006 | Ying |
| 7,136,451 B2 | 11/2006 | Naidu |
| 7,139,406 B2 | 11/2006 | Le |
| 7,142,628 B2 | 11/2006 | Grass |
| 7,149,278 B2 | 12/2006 | Arenson et al. |
| 7,149,339 B2 | 12/2006 | Veneruso |
| 7,158,611 B2 | 1/2007 | Heismann |
| 7,164,747 B2 | 1/2007 | Ellenbogen |
| 7,164,750 B2 | 1/2007 | Nabors |
| 7,166,458 B2 | 1/2007 | Ballerstadt |
| 7,167,539 B1 | 1/2007 | Hoffman |
| 7,173,998 B2 | 2/2007 | Hoffman |
| 7,177,387 B2 | 2/2007 | Yasunaga |
| 7,177,391 B2 | 2/2007 | Chapin |
| 7,192,031 B2 | 3/2007 | Dunham |
| 7,197,113 B1 | 3/2007 | Katcha |
| 7,206,379 B2 | 4/2007 | Lemaitre |
| 7,215,731 B1 | 5/2007 | Basu |
| 7,218,704 B1 | 5/2007 | Adams |
| 7,224,763 B2 | 5/2007 | Naidu |
| 7,224,765 B2 | 5/2007 | Ellenbogen |
| 7,224,769 B2 | 5/2007 | Turner |
| 7,233,640 B2 | 6/2007 | Ikhlef |
| 7,236,564 B2 | 6/2007 | Hopkins |
| 7,238,945 B2 | 7/2007 | Hoffman |
| 7,251,310 B2 | 7/2007 | Smith |
| 7,260,170 B2 | 8/2007 | Arenson |
| 7,260,171 B1 | 8/2007 | Arenson |
| 7,260,172 B2 | 8/2007 | Arenson |
| 7,260,174 B2 | 8/2007 | Hoffman |
| 7,260,182 B2 | 8/2007 | Toth et al. |
| 7,263,160 B2 | 8/2007 | Schlomka |
| 7,266,180 B1 | 9/2007 | Saunders |
| 7,272,429 B2 | 9/2007 | Walker |
| 7,274,767 B2 | 9/2007 | Clayton |
| 7,277,577 B2 | 10/2007 | Ying |
| 7,279,120 B2 | 10/2007 | Cheng |
| 7,280,631 B2 | 10/2007 | De Man et al. |
| 7,283,604 B2 | 10/2007 | De Man et al. |
| 7,283,609 B2 | 10/2007 | Possi et al. |
| 7,295,651 B2 | 11/2007 | Delgado |
| 7,298,812 B2 | 11/2007 | Tkaczyk |
| 7,302,083 B2 | 11/2007 | Larson |
| 7,308,073 B2 | 12/2007 | Tkaczyk |
| 7,308,077 B2 | 12/2007 | Jiang |
| 7,317,390 B2 | 1/2008 | Huey et al. |
| 7,324,625 B2 | 1/2008 | Eilbert |
| 7,327,853 B2 | 2/2008 | Ying |
| 7,330,535 B2 | 2/2008 | Hoffman |
| 7,333,589 B2 | 2/2008 | Ellenbogen et al. |
| 7,336,769 B2 | 2/2008 | Verbinski |
| 7,430,270 B2 | 9/2008 | Bontus |
| 7,558,364 B2 | 7/2009 | Lin |
| 7,697,658 B2 | 4/2010 | Wang |
| 7,706,499 B2 | 4/2010 | Pack |
| 7,778,387 B2 | 8/2010 | Koehler |
| 7,933,375 B2 | 4/2011 | Pack |
| 8,050,480 B2 | 11/2011 | Noo |

(56) References Cited

U.S. PATENT DOCUMENTS

| | | | |
|---|---|---|---|
| 8,804,899 B2* | 8/2014 | Morton | 378/9 |
| 2001/0029334 A1 | 10/2001 | Graumann | |
| 2001/0038681 A1 | 11/2001 | Stanton | |
| 2002/0031202 A1 | 3/2002 | Callerame | |
| 2002/0034276 A1 | 3/2002 | Hu | |
| 2002/0075545 A1 | 6/2002 | Harrison | |
| 2002/0176531 A1 | 11/2002 | McClelland | |
| 2003/0021377 A1 | 1/2003 | Turner | |
| 2003/0103212 A1 | 6/2003 | Westphal | |
| 2003/0128869 A1 | 7/2003 | Grass | |
| 2004/0017888 A1 | 1/2004 | Seppi | |
| 2004/0066879 A1 | 4/2004 | Machida | |
| 2004/0101086 A1 | 5/2004 | Sabol | |
| 2004/0109532 A1 | 6/2004 | Ford | |
| 2004/0170254 A1 | 9/2004 | Gregerson | |
| 2004/0179643 A1 | 9/2004 | Gregerson | |
| 2004/0213378 A1 | 10/2004 | Zhou | |
| 2004/0240603 A1 | 12/2004 | Cai | |
| 2004/0252807 A1 | 12/2004 | Skatter | |
| 2004/0258305 A1 | 12/2004 | Burnham | |
| 2005/0031075 A1 | 2/2005 | Hopkins | |
| 2005/0053189 A1 | 3/2005 | Gohno | |
| 2005/0105682 A1 | 5/2005 | Heumann | |
| 2005/0111610 A1 | 5/2005 | Heumann | |
| 2005/0123089 A1 | 6/2005 | Man | |
| 2005/0123092 A1 | 6/2005 | Mistretta | |
| 2005/0157925 A1 | 7/2005 | Lorenz | |
| 2005/0169423 A1 | 8/2005 | Ellenbogen | |
| 2005/0226364 A1 | 10/2005 | Bernard | |
| 2005/0249432 A1 | 11/2005 | Zou | |
| 2005/0281390 A1 | 12/2005 | Johnson | |
| 2006/0018428 A1 | 1/2006 | Li | |
| 2006/0050642 A1 | 3/2006 | Wang | |
| 2006/0050842 A1 | 3/2006 | Wang | |
| 2006/0104410 A1 | 5/2006 | Sauer | |
| 2006/0113163 A1 | 6/2006 | Hu | |
| 2006/0116567 A1 | 6/2006 | Nilsen | |
| 2006/0273259 A1 | 12/2006 | Li | |
| 2006/0291612 A1 | 12/2006 | Nishide | |
| 2007/0019779 A1 | 1/2007 | Nishide | |
| 2007/0053495 A1 | 3/2007 | Morton | |
| 2007/0096030 A1 | 5/2007 | Li | |
| 2007/0110215 A1 | 5/2007 | Hu | |
| 2007/0172024 A1 | 7/2007 | Morton | |
| 2007/0183568 A1 | 8/2007 | Kang | |
| 2008/0056436 A1 | 3/2008 | Pack | |
| 2009/0128557 A1 | 5/2009 | Finlayson | |
| 2009/0252295 A1* | 10/2009 | Foland | 378/98.12 |
| 2010/0303329 A1 | 12/2010 | Morton | |
| 2011/0091007 A1 | 4/2011 | Betcke | |

FOREIGN PATENT DOCUMENTS

| | | | |
|---|---|---|---|
| EP | 0531993 A1 | 3/1993 | |
| EP | 0584871 A1 | 3/1994 | |
| EP | 0924742 A2 | 6/1999 | |
| EP | 0930046 A2 | 7/1999 | |
| EP | 1277439 A1 | 1/2003 | |
| EP | 1374776 A1 | 1/2004 | |
| FR | 2328280 A1 | 5/1977 | |
| GB | 1497396 A | 1/1978 | |
| GB | 1526041 A | 9/1978 | |
| GB | 2015245 A | 9/1979 | |
| GB | 2089109 A | 6/1982 | |
| GB | 2212903 A | 8/1989 | |
| GB | 2356453 A | 5/2001 | |
| GB | 2437777 A | 11/2007 | |
| JP | 570175247 | 10/1982 | |
| JP | 600015546 | 1/1985 | |
| JP | 600021440 | 2/1985 | |
| JP | H10211196 A | 8/1998 | |
| JP | 2001176408 A | 6/2001 | |
| JP | 2004079128 A | 3/2004 | |
| WO | 9528715 A2 | 10/1995 | |
| WO | 9960387 A2 | 11/1999 | |
| WO | 03051201 A2 | 6/2003 | |
| WO | 03105159 | 12/2003 | |
| WO | 2004097889 A2 | 11/2004 | |
| WO | 2004111625 | 12/2004 | |
| WO | 2005084351 | 9/2005 | |
| WO | 2006135586 | 12/2006 | |

OTHER PUBLICATIONS

EPO Application No. 10184996.6, Search Report, Dec. 27, 2010, Rapiscan Security Products, Inc.

International Search Report, PCT/US2010/036179, Aug. 30, 2010, Rapiscan Security Products, Inc.

International Search Report, PCT/GB2004/001729, Aug. 12, 2004, Rapiscan Systems, Inc.

International Search Report, PCT/GB2004/001741, Mar. 3, 2005.

International Search Report, PCT/GB2004/001731, May 27, 2005.

International Search Report, PCT/GB2004/001732, May 27, 2005.

International Search Report, PCT/GB2004/001751, Mar. 21, 2005.

International Search Report, PCT/GB2004/001747, Aug. 10, 2004.

Development of ultra-fast X-ray computed tomography scanner system, INS 98-43 6068772 A9823-8760J-016 (PHA); B9812-7510B-113 (EEA) NDN-174-0606-8771-7, Hori, K.; Fujimoto, T.; Kawanishi, K., Editor—Nalcioglu, O., Abbreviated Journal Title—1997 IEEE Nuclear Science Symposium, Conference Record (Cat. No. 97CH36135),(Part No. vol. 2, 1997, pp. 1003-1008 vol. 2, 2 vol. xlviii+1761 page(s), ISBN-0 7803 4258 5.

Yu et al., A Rebinning-type Backprojection-Filtration Algorithm for Image Reconstruction in Helical Cone-beam CT, IEEE Nuclear Science Symposium Conference Record, 2006, pp. 2869-2872Zo.

Zou et al., Theory and algorithms for image reconstruction on chords and within region of interest, J. Opt Soc Am A, vol. 22, No. 11, Nov. 2005, pp. 2372-2384.

International Search Report, PCT/US2010/41871, Jan. 20, 2011, Rapiscan Systems, Inc.

Rebinning-Based Algorithms for Helical Cone-Beam CT, Defrise et al., IOP Publishing, 2911-2937, 2001.

* cited by examiner

IMAGING, DATA ACQUISITION, DATA TRANSMISSION, AND DATA DISTRIBUTION METHODS AND SYSTEMS FOR HIGH DATA RATE TOMOGRAPHIC X-RAY SCANNERS

CROSS-REFERENCE TO RELATED APPLICATIONS

The present application relies on U.S. Patent Provisional Application No. 61/181,077 filed on May 26, 2009, for priority.

The present application is also a continuation-in-part of U.S. patent application Ser. No. 12/485,897, filed on Jun. 16, 2009, which is a continuation of U.S. patent application Ser. No. 10/554,656, filed on Oct. 25, 2005, and now issued U.S. Pat. No. 7,564,939, which is a 371 national stage application of PCT/GB04/01729, filed on Apr. 23, 2004 and which, in turn, relies on Great Britain Application No. 0309387.9, filed on Apr. 25, 2003, for priority.

The present application is also a continuation-in-part of U.S. patent application Ser. No. 12/371,853, filed on Feb. 16, 2009, which is a continuation of U.S. patent application Ser. No. 10/554,975, filed on Oct. 25, 2005, and now issued U.S. Pat. No. 7,512,215, which is a 371 national stage application of PCT/GB2004/01741, filed on Apr. 23, 2004 and which, in turn, relies on Great Britain Application Number 0309383.8, filed on Apr. 25, 2003, for priority.

The present application is also a continuation-in-part of U.S. patent application Ser. No. 12/651,479, filed on Jan. 3, 2010, which is a continuation of U.S. patent application Ser. No. 10/554,654, filed on Oct. 25, 2005, and now issued U.S. Pat. No. 7,664,230, which is a 371 national stage application of PCT/GB2004/001731, filed on Apr. 23, 2004 and which, in turn, relies on Great Britain Patent Application Number 0309371.3, filed on Apr. 25, 2003, for priority.

The present application is also a continuation-in-part of U.S. patent application Ser. No. 12/364,067, filed on Feb. 2, 2009, which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority.

The present invention is also a continuation-in-part of U.S. patent application Ser. No. 12/758,764, filed on Apr. 12, 2010, which is a continuation of U.S. patent application Ser. No. 12/211,219, filed on Sep. 16, 2008, and now issued U.S. Pat. No. 7,724,868, which is a continuation of U.S. patent Ser. No. 10/554,655, filed on Oct. 25, 2005, and now issued U.S. Pat. No. 7,440,543, which is a 371 national stage application of PCT/GB2004/001751, filed on Apr. 23, 2004, and which, in turn, relies on Great Britain Patent Application Number 0309385.3, filed on Apr. 25, 2003, for priority.

The present application is also a continuation-in-part of U.S. patent application Ser. No. 12/697,073, filed on Jan. 29, 2010, which is a continuation of U.S. patent application Ser. No. 10/554,570, filed on Oct. 25, 2005, and now issued U.S. Pat. No. 7,684,538, which is a 371 national stage application of PCT/GB2004/001747, filed on Apr. 23, 2004, and which, in turn, relies on Great Britain Patent Application Number 0309379.6, filed on Apr. 25, 2003, for priority.

The present application is also a continuation-in-part of U.S. patent application Ser. No. 12/097,422, filed on Jun. 13, 2008, and U.S. patent application Ser. No. 12/142,005, filed on Jun. 19, 2008, both of which are 371 national stage applications of PCT/GB2006/004684, filed on Dec. 15, 2006, which, in turn, relies on Great Britain Patent Application Number 0525593.0, filed on Dec. 16, 2005, for priority.

The present application is also a continuation-in-part of U.S. patent application Ser. No. 12/478,757, filed on Jun. 4, 2009, which is a continuation of U.S. patent application Ser. No. 12/364,067, filed on Feb. 2, 2009, which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority. In addition, U.S. patent application number relies on Great Britain Patent Application Number 0812864.7, filed on Jul. 15, 2008, for priority.

The present application is also a continuation-in part of U.S. patent application Ser. No. 12/712,476, filed on Feb. 25, 2010, which relies on U.S. Provisional Patent Application No. 61/155,572 filed on Feb. 26, 2009 and Great Britain Patent Application No. 0903198.0 filed on Feb. 25, 2009, for priority.

Each of the aforementioned PCT, foreign, and U.S. applications, and any applications related thereto, is herein incorporated by reference in their entirety.

BACKGROUND OF THE INVENTION

Applicant has developed a new generation of X-ray systems that implement X-ray sources with more than one electron gun and one or more high voltage anodes within a single vacuum envelope.

The rapid switching of electron guns under electrostatic control enables the fast movement of the effective focal spot of the X-ray tube and the rapid generation of sets of tomographic X-ray scan data without the use of moving parts. By configuring the firing sequence of the electron guns appropriately, an optimal set of X-ray projection data can be collected at rates far higher than in conventional systems.

Accordingly, because Applicant's latest generation X-ray tomography systems are capable of generating very high resolution tomography X-ray data at high speeds, a number of new data acquisition and data transmission and distribution systems are enabled, and/or required, to take full advantage of, and/or optimally manage, these high data rate systems. For example, current storage systems and data transmission networks are unable to effectively transfer high volumes of image data to network of operator workstations without undue delay. Moreover, such delay increases as the number of image generating systems on a network increases and as the number of operators required to analyze images also increases.

Therefore, improved data acquisition, transmission and distribution systems are needed to take full advantage of, and/or optimally manage, high resolution X-ray data generated at high speeds, such as data rates greater than 1 Gbit/second.

SUMMARY OF THE INVENTION

In an embodiment, the present invention provides an X-ray system comprising: a source-detector module comprising a plurality of X-ray sources and detectors for scanning an object being inspected; a scan engine coupled to the source-detector module for collecting scan data from the source detector module; an image reconstruction engine coupled to the scan engine for converting the collected scan data into one or more X-ray images; and a scan controller coupled with at least one of the source detector module, the scan engine, and the image reconstruction engine, and a user input module for providing control information based on at least one of: user constraints obtained via the user input module, the scan data and the X-ray image data, the control information optimizing operations of the X-ray system dynamically. The X-ray system further comprises a data visualisation engine coupled to the image reconstruction engine for rendering the image data to a human readable screen and one or more storage devices coupled to one or more of the source detector module, the scan engine, and the image reconstruction engine for storing data obtained therefrom.

In an embodiment, the scan engine co-ordinates the source-detector module, and is programmable on a scan-by-scan basis and within a scan, thereby allowing for rapid re-optimization of the source-detector module. The scan controller optimizes the scan engine by analyzing the scan data for identifying one or more regions comprising required information, and controlling the scan engine to collect scan data only from the X-ray sources and detectors corresponding to the one or more identified regions. In an embodiment, the scan data is analyzed by using a sinogram chart to obtain a region of interest, the sinogram chart comprising data from each detector arranged in a horizontal row and data from each X-ray source rotation angle arranged in consecutive rows to form a two dimensional data set, and the region of interest is obtained by obtaining a trajectory thorough the sinogram data set corresponding to at least two required points in the object being inspected.

In an embodiment, the scan controller optimizes the image reconstruction engine by providing control information directing the image reconstruction engine to convert only a predefined portion of scan data into an X-ray image. Further, the scan controller controls the scan engine to generate a first spatial resolution in a scan direction and a second spatial resolution in a scan plane, the first spatial resolution being lower than the second spatial resolution. Also, the scan controller controls the spatial resolution of the scan data collected by the scan engine dynamically, the controlled data being passed to the image reconstruction engine for generating variable resolution image data.

In another embodiment, the present invention provides an image transmission system comprising: a plurality of X-ray systems for inspecting one or more object by using X-rays and producing at least one three-dimensional (3D) image of each object; a plurality of 3D engines, each 3D engine being coupled with at least one X-ray system for obtaining one or more two dimensional (2D) images by processing each 3D image produced by the X-ray system, the 2D images being projections of the 3D image; at least one network scheduler coupled to each 3D engine via a dedicated network link for rendering the one or more 2D images to one or more operators for manual inspection, each operator inspecting a 2D image for obtaining one or more predefined features, the network scheduler rendering a corresponding 3D image to an operator for inspection upon receiving a request for the same; and at least one storage array coupled with each of the X-ray systems via a high speed dedicated network link for storing one or more of the 3D images and the 2D images.

In another embodiment, the present invention is directed toward an image transmission system comprising a plurality of X-ray systems for inspecting one or more object by using X-rays and producing at least one three-dimensional image of each object; a plurality of engines, each engine being coupled with at least one X-ray system for obtaining one or more two dimensional images by processing each image produced by the X-ray system, the two dimensional images being projections of the three dimensional image; at least one network scheduler coupled to each three dimensional engine via a network link for rendering the one or more two dimensional images to one or more operators for manual inspection, wherein the network scheduler renders a corresponding three dimensional image to an operator for inspection upon receiving a request for such three dimensional image; and at least one storage array coupled with each of the X-ray systems via a high speed dedicated network link for storing one or more of the three dimensional images and the two dimensional images.

In another embodiment, the present invention is directed toward an X-ray system comprising a plurality of detectors for generating raw X-ray data; a scan engine coupled to the plurality of detectors for receiving the raw X-ray data and generating calibrated X-ray data; an image reconstruction engine coupled to the scan engine for converting the calibrated X-ray data into one or more processed X-ray images; and a scan controller coupled with said plurality of detectors and at least one of said scan engine or image reconstruction engine, wherein said scan controller receives said raw X-ray data and dynamically modulates processing of at least one of said raw X-ray data by said scan engine or said calibrated X-ray data by said image reconstruction engine.

The X-ray system further comprises a user input wherein said user input receives control information from a user and wherein said scan controller uses said control information to dynamically modulate processing of at least one of said raw X-ray data by said scan engine or processing of said calibrated X-ray data by said image reconstruction engine. The raw X-ray data is transmission data. The raw X-ray data is backscatter data. The X-ray system further comprises a data visualization engine coupled to the image reconstruction engine for rendering the processed X-ray images to a human readable screen. The X-ray system further comprises one or more storage devices coupled to one or more of the plurality of detectors, the scan engine, and the image reconstruction engine for storing data obtained from the plurality of detectors, the scan engine, and the image reconstruction engine.

The scan controller dynamically modulates the processing of said raw X-ray data by said scan engine by analyzing the raw X-ray data and identifying one or more regions comprising required information. The one or more regions comprising required information is a subset of all regions detected by said plurality of detectors, e.g. not all regions contain required information and only those regions that do are subjected to calibration or image processing.

The scan controller issues instructions to the scan engine to process raw X-ray data only from detectors corresponding to the one or more regions comprising required information. The scan controller issues instructions to the image reconstruction engine to process calibrated X-ray data only from detectors corresponding to the one or more regions comprising required information. The X-ray system further comprises a data visualization engine wherein said data visualization engine receives from said image reconstruction engine a plurality of coordinates corresponding to the one or more regions comprising required information.

In another embodiment, the X-ray system comprises a source of radiation having a scan rotation; a plurality of detectors for generating raw X-ray data; a scan engine coupled to the plurality of detectors for receiving the raw X-ray data and generating calibrated X-ray data; an image reconstruction engine coupled to the scan engine for converting the calibrated X-ray data into one or more processed X-ray images; and a scan controller coupled with said plurality of detectors and at least one of said scan engine or image reconstruction engine, wherein said scan controller receives said raw X-ray data and dynamically modulates at least one of said source of radiation or scan engine based on said raw X-ray data. The scan controller issues instructions to said scan engine to modify a spatial resolution of a scan based upon said raw X-ray data. The spatial resolution is modified by generating a first spatial resolution in a scan direction and a second spatial resolution in a scan plane, the first spatial resolution being different than the second spatial resolution.

The scan controller issues instructions to said scan engine to generate a first resolution in a scan and a second resolution in the scan wherein said first resolution and said second resolution are different. The scan engine transmits said scan having the first resolution and the second resolution to the image reconstruction engine. The image reconstruction engine generates image data having variable resolution based on said scan having the first resolution and the second resolution. The image reconstruction engine generates image data having at least one area of coarse pixelation, medium granularity pixelation, or high granularity pixelation. The scan controller issues instructions to at least one of said scan engine or source of radiation to control a rotation rate of said source of radiation.

DETAILED DESCRIPTION OF THE INVENTION

The X-ray systems disclosed in the above-mentioned applications, which are herein incorporated by reference, enable the rapid and real-time control of X-ray source trajectories. The present invention takes advantage of this capability by dynamically controlling X-ray source trajectories and dynamically altering the image reconstruction methods based on both the properties of the object under investigation and the quality of the inspection decision that is required. This dynamic system optimization can have several benefits, including reduction of scan dose, reduction of computation complexity and reduction of data bandwidth. Other objectives can be addressed using the same and related optimization methods.

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
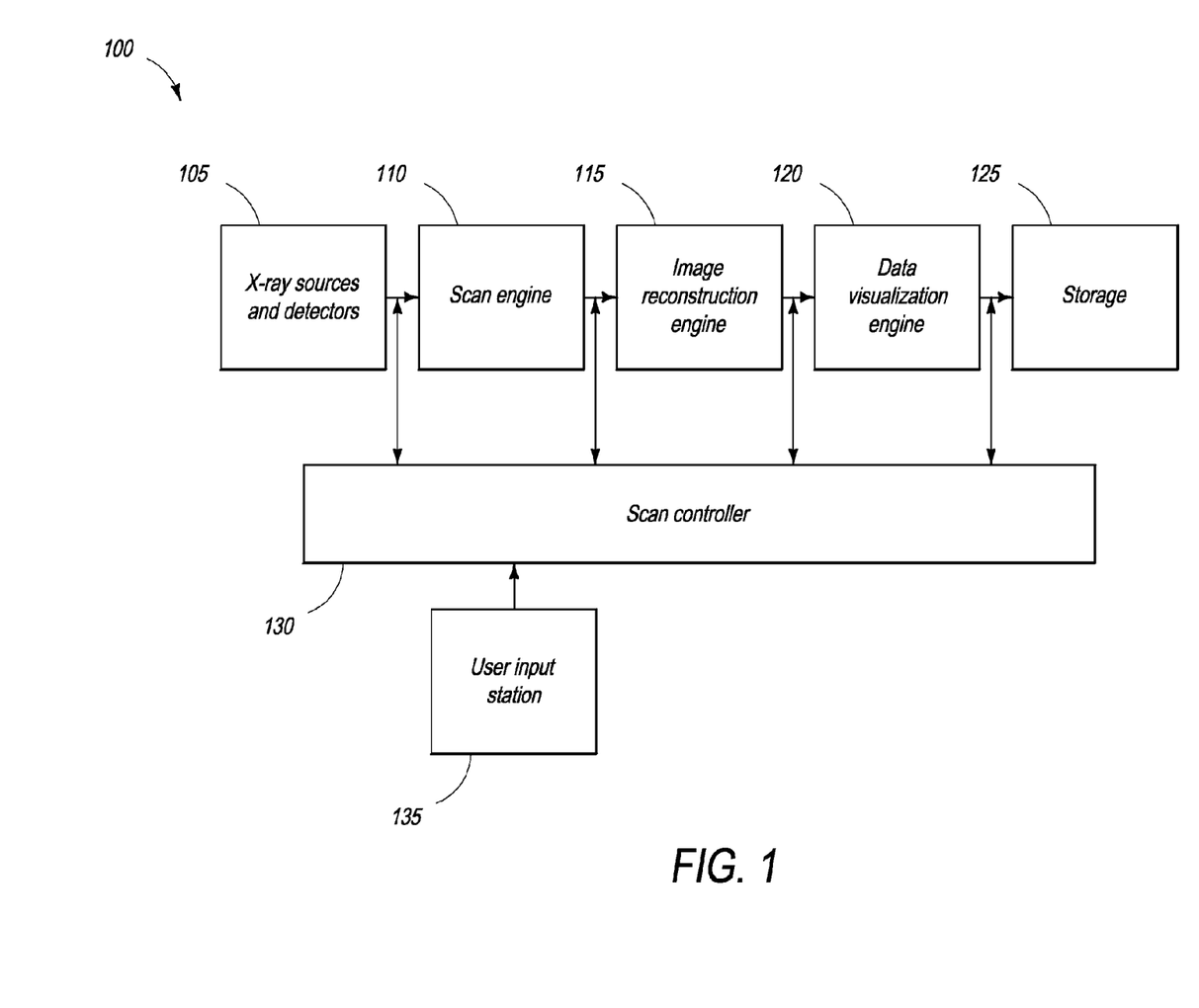
FIG. 1 is a block diagram of one embodiment of the X-ray system of the present invention.

The present invention will now be discussed in context of embodiments as illustrated in the accompanying drawings. Referring to FIG. 1, one embodiment of an X-ray system configuration is shown. The X-ray system 100 comprises a set of X-ray sources and X-ray detectors 105 which are capable of collecting information about the object under inspection. The set of sources and detectors (sensors) 105, are, in one embodiment configured to generate transmitted X-ray data set suitable for tomographic image reconstruction. Alternatively, in another embodiment, the set of sources and sensors 105 are configured to generate a set of diffraction X-ray data or a set of backscattered X-ray data. Alternatively, in yet another embodiment, sources and sensors 105 are configured to generate a set of stereoscopic transmission X-ray data. One of ordinary skill in the art would appreciate that the present invention can be applied to other source and sensor geometries.

As shown in FIG. 1, a scan engine 110 coordinates scanning of the object under inspection and data collection from the X-ray sources and detectors 105. The scan engine 110 is programmable on a scan-by-scan basis and also within a scan to allow rapid re-optimization of the X-ray system 100.

As shown in FIG. 1, an image reconstruction engine 115 takes the raw data and/or calibrated data which is output from the scan engine 110 and converts this data into a recognizable set of image data or processed data. It should be appreciated that calibrated data can be generated from a pre-processor which is part of the scan engine 110 and which can also be considered the first stage of the image reconstruction engine 115.

For example, suppose that the scan engine 110 normally provides a set of calibrated transmission X-ray projection data. The image reconstruction engine 115 takes this projection data and converts this data into an X-ray image using a plurality of processing techniques such as filtered back projection to convert the projection data back into a 2- or 3-dimensional tomographic X-ray image. As used herein, raw data refers to data directly transferred from one or more detectors or detector data that has not yet been subject to calibration or normalization. Raw data which has been subject to calibration or normalization is referred to as calibrated data. Processed data or image data is calibrated data that has been passed through one or more filters.

Processed data from the image reconstruction engine 115 is optionally passed to an optional data visualization engine 120. The data visualisation engine 120 takes the reconstructed image data and renders it to a human readable screen. This data visualization engine 120, in one embodiment, is capable of performing functions such as interpolation, three-dimensional projection into a two-dimensional image, and image coloring based on reconstructed image density, materials type or other parameters as required.

In one embodiment, a storage device 125, such as a RAID array, set of hard disks, or other memory systems, is provided for archiving X-ray image data. It will be understood by an expert that the storage device 125 shall be capable of storing data from any point in the signal chain, and not just at the output of the data visualisation engine.

The scan controller 130 is capable of interpreting X-ray image data at the output from all components in the imaging chain. The scan controller 130 is also capable of outputting control information to all components in the imaging chain. In this way, the scan controller 130 has the ability to optimize the entire system operation.

The scan controller 130 also receives input data from a user input station 135, in which users can input their constraints on the image optimization process via, for example, a touch screen, mouse, or keyboard in communication with a computing device. For example, in a security screening system the user may select a current threat level (e.g. High, Medium or Low). In a medical system, the user may select a dose or spatial resolution constraint (e.g. High Diagnostic Quality, Low Dose).

The scan controller 130 thus takes input from two different sources, namely user constraints and X-ray image data, and implements a method which processes the X-ray image data according to the user constraints in order to continually and dynamically re-optimize the operation of the X-ray sources and detectors 105, the scan engine 110, the image reconstruction engine 115, and/or the data visualisation engine 120.

It should be appreciated that the functions and features of the X-ray sources and detectors 105, scan engine 110, image reconstruction engine 115, and/or data visualization engine 120, as described herein, are enabled by hardware, such as servers comprising at least one processor, executing a plurality of programmatic instructions which are stored in a memory, such as RAM, ROM, hard disk, or other memory structures. The various engines may be integrated into one or more servers which are remote or local to one another. The components of the X-ray system 100 may therefore be local or remote from each other, may be integrated into a single server or distributed among a plurality of servers across a network, and/or may communicate with each other through any wired or wireless form of transmission and reception. It should further be appreciated that each engine comprises at least one data receiver, data transmitter, and data processor capable of executing a plurality of programmatic instructions, stored in memory, to perform the functions and features of the engines, as described herein.

Figure 2:
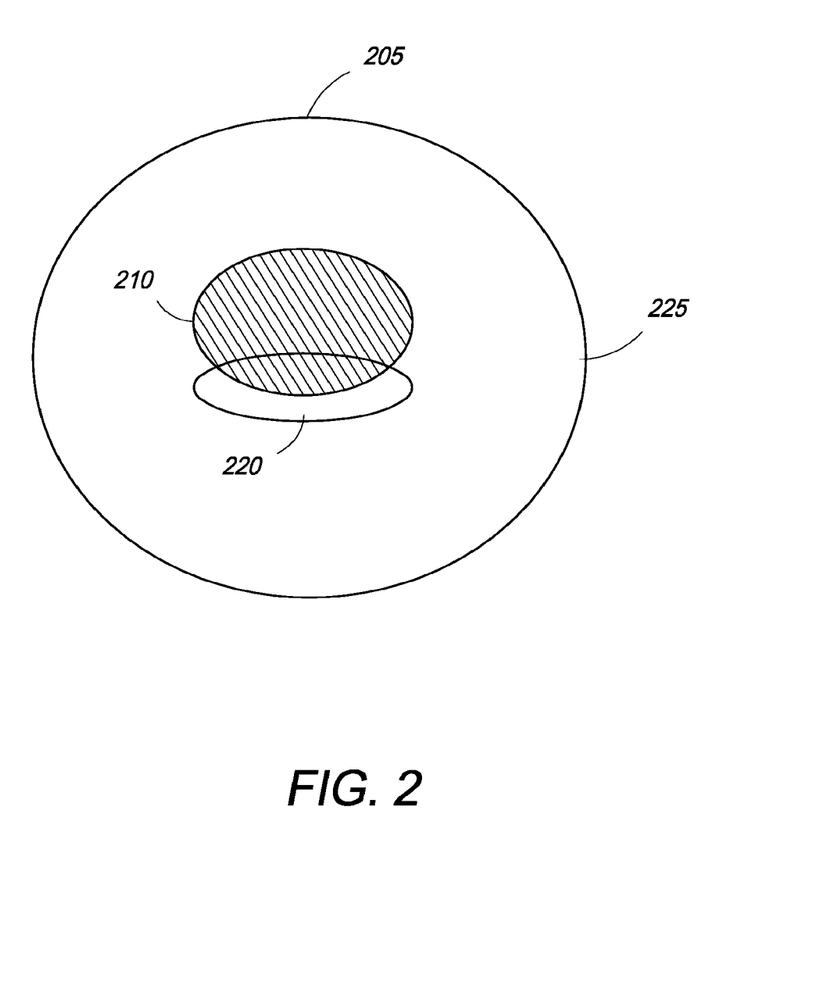
FIG. 2 depicts an imaging area relative to the object being inspected.

Referring to FIG. 2, in one embodiment, the tomographic X-ray imaging system of the present invention images an object 210 which partially fills the imaging area 205. Conventionally, a rotating gantry X-ray source is used and projection data is accumulated for all projection angles and from all detector elements. It is computationally expensive to collect and process all of this data when only a fraction of the X-ray inspection area is actually filled with a relevant object. The fraction of the X-ray inspection area which is filled with air 225 or the object support 220 is generally of little interest to the user.

Figure 3:
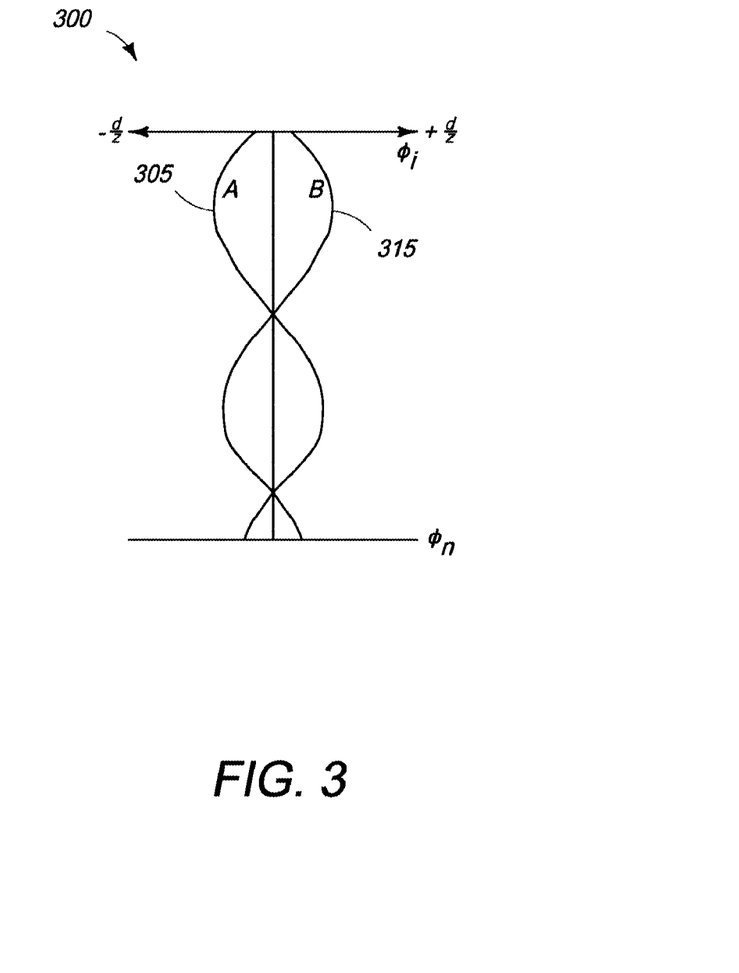
FIG. 3 depicts an exemplary sinogram generated by the present invention.

In one embodiment, this scanning scenario can be improved in the following manner. Rather than scan and process the entire imaging area 205, raw scan data generated by the X-ray system is first analyzed by the scan controller 130. Regions of the image data that contain relevant information are differentiated from those areas which contain no relevant data. As shown in FIG. 3, a sinogram chart 300 can be used to review the data. The chart 300 arranges data from each detector in a horizontal row (from −d/2 through 0 to +d/2 where d=total number of detectors in a projection) and data from each source rotation angle (from Phi_1 to Phi_n where n=number of projection angles) in consecutive rows to form a two dimensional data set. The trajectory thorough the sinogram data set for two points in the object, labelled A 305 and B 315, is also shown in the diagram.

In the present invention, once the first line of the sinogram (Phi_1) has been collected, it is known, a priori, what part of the sinogram will need to be collected at all other projections angles. The scan controller can therefore optimize the scan engine to only collect and process data from those detector elements which are actually needed, e.g. would actually generate relevant data, thereby saving on front end data bandwidth and computer power.

Mathematically, the sinogram data is linked forward to the backprojected image by the Radon Transform. Under this transform, each point in the sinogram represents one backprojected line through the reconstructed image. Since it is known which parts of the sinogram contain useful data, and hence were collected by the scan engine, the image reconstruction engine is therefore constrained to only filter and backproject the valuable parts of the sinogram data. This can yield major savings in computational cost in the image reconstruction engine.

The image reconstruction engine is typically designed to permit full image reconstruction of the whole image reconstruction circle at full reconstructed image slice rate. Very often, only a fraction of the image reconstruction circle has an object therein, and systems designed with the use of the scan controller can be provided with a much lower cost image reconstruction engine that is optimized to dynamically reconstruct only the relevant part of the object. Preferably, the scan engine and image reconstruction engine shall comprise, or have access to, a buffer memory to allow sequences of images where the object is larger than the designed image reconstruction circle fill capacity to be stored temporarily until the image reconstruction engine has caught up with the current data flow.

The data visualisation engine is provided with the coordinates (such as slice number and position within the slice) of the sub-image which is provided by the image reconstruction engine and it uses these coordinates (slice number and position within the slice) to reference the reconstructed image data to the appropriate part of the three-dimensional reconstructed image volume prior to data visualization. The net effect is a substantial reduction in data bandwidth to the storage system. This simplifies design of network attached storage and reduces the cost of storage solutions since unwanted background data is not stored.

In a further example of the use of this invention, it may be the case that the object to be inspected has variable inspection significance along its length. For example, some parts of the human body are quite symmetric in the scan direction (the legs) and here it may be advantageous to design a tomographic image system which generates a lower spatial resolution in the scan direction (along the legs) compared to that in the scan plane.

Figure 4:
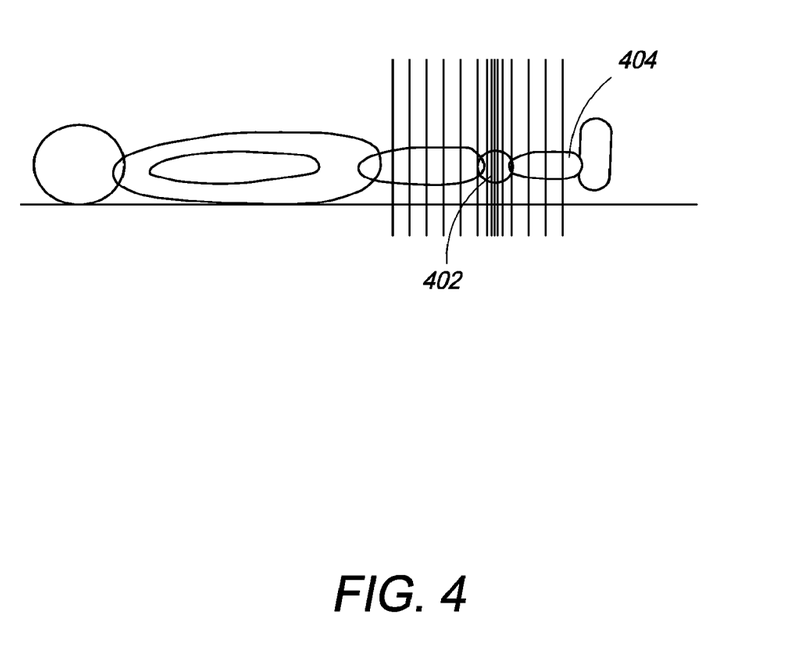
FIG. 4 depicts a variable scan, based on the object being scanned.

To do this, the user may request the scan controller to use a low dose scanning method, which could be achieved by dynamically controlling the scan rotation rate to allow a degree of scan-direction partial volume artifact when imaging the long bones of the leg in order to reduce dose. Referring to FIG. 4, when arriving at the knees 402 which are substantially variable in the scan direction, the scan controller can automatically direct the scan engine to increase scan rate (and hence also X-ray dose) in order to create a high-resolution image of the knees 402 prior to returning to a lower dose rate once back to the long bones 404 past the knee.

Mathematically, the scan controller can determine the rate of change of information in the scan direction by subtracting each new sinogram from the previous sinogram and the difference is an indication of the rate of change of information in the scan direction.

In a further embodiment of this invention, it is possible to use the scan controller to adjust, on a dynamic basis, the spatial resolution in the data collected by the scan engine. This data is then passed through to the image reconstruction engine which in turn provides a variable resolution image. The reconstructed image is encoded for display by the data visualization engine so that the image is represented correctly in both the spatial and time domains.

Figure 5:
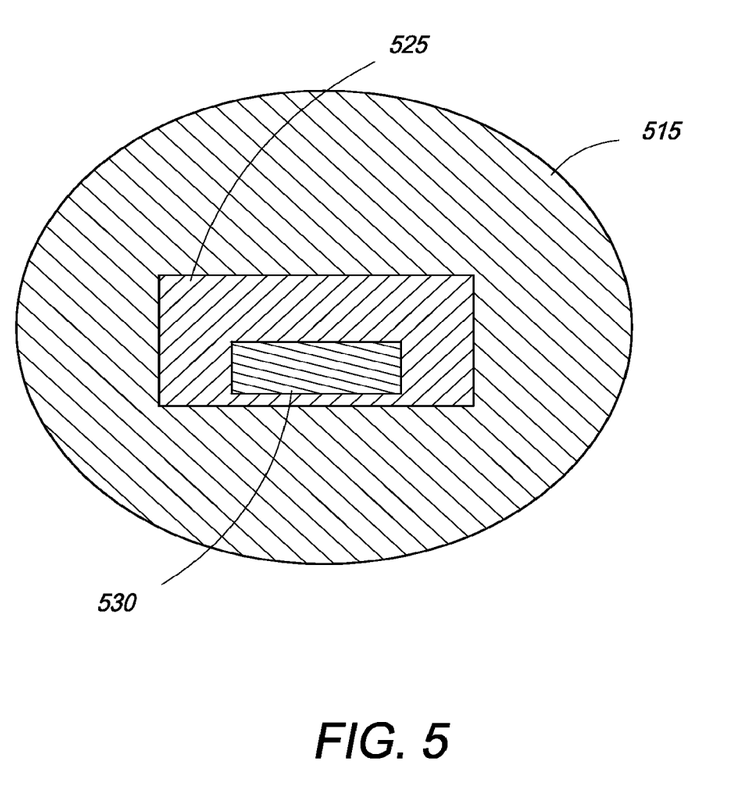
FIG. 5 is an exemplary diagram of variable pixelation levels of an object being scanned.

As an example, in a security inspection application providing three-dimensional tomographic image reconstruction, one can reconstruct low density regions, such as clothes, with coarse pixelation 515 (such as greater than ten times the smallest pixel size), reserving medium granularity pixelation 525 (such as 2-10 times the smallest pixel size) and high granularity pixelation 530 (such as the smallest pixel size, i.e. 1 mm×1 mm) for complex objects, such as a lap-top computer, which resembles a higher-threat object, as shown in FIG. 5. By relaxing the resolution requirements in some areas, and thus requiring less computation, the spare computation capacity can be allocated to provide enhanced resolution in complex areas of the image. The net effect is a reduction in data bandwidth, a reduction in computational cost and a reduction in storage requirements with little detriment to diagnostic quality.

In one embodiment, the sinogram data directs the scan controller regarding what computational power should be allocated in order to form the reconstructed image. Sinogram regions that exhibit a high degree of variation, such as those regions with a smaller signal to noise ratio (i.e. a ratio of less than 20, preferably less than 10), are linked directly to those areas of the reconstructed image where a high image resolution should be achieved. A high image resolution is typically less than 2 mm×2 mm×2 mm in terms of pixel size, while a low image resolution is typically greater than 5 mm×5 mm×5 mm in terms of pixel size. Regions of the sinogram that exhibit a low degree of variation, such as those regions with a higher signal to noise ration (i.e. a ratio of greater than 40, preferably greater than 50), are linked to those areas of the reconstructed image where a low image resolution can be tolerated.

One of ordinary skill in the art would appreciate that the variable resolution reconstructed image should be encoded such that the data visualization engine can reference the variable resolution reconstructed image data into the appropriate locations in the three-dimensional data set for human display purposes. It is further understood that suitable image processing methods, such as three-dimensional image interpolation, can be used to render an image with uniformly high spatial resolution to the screen even though the underlying data may have been reconstructed at variable resolution.

In a further embodiment of this invention, it is recognized that the nature of the image reconstruction process itself can be affected by the information that is being processed by the scan engine. By way of example, consider an imaging system which is typically looking for low atomic number, low contrast objects in a uniform matrix. Such an image is suited to a filtered backprojection tomographic image reconstruction approach. Suppose that there is, from time to time, a contaminant that is of high atomic number which enters the imaging volume. In this case, the high atomic number material is likely to result in unwanted beam hardening artifact which can distort the analysis of the low atomic number materials. There are known iterative processes which are better at minimizing the effect of beam hardening than typical filtered backprojection algorithms. In this case, the scan controller can inspect the sinogram for particularly highly attenuating objects and can substitute iterative algorithms for those regions where the highly attenuating objects are located, and can apply the less computationally demanding filtered backprojection algorithm to all other areas of the image. The result is a minimization in beam hardening artifact and an improvement in ultimate image analysis.

It shall be evident to one skilled in the art that it is possible to apply the methods described here simultaneously and individually depending on the optimization requirements that have been set by the user, on the cost constraints that were evaluated at the time of system manufacture, and on the availability and performance of storage systems.

Figure 6:
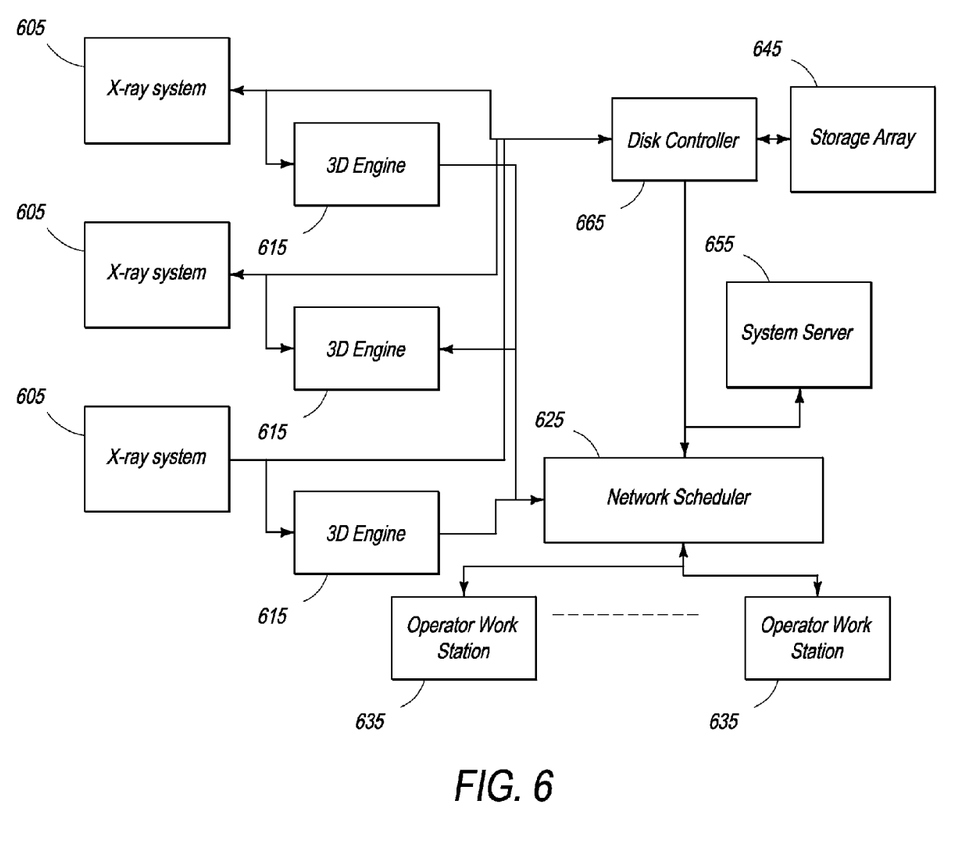
FIG. 6 is a diagram of a collection of X-ray systems with improved data transmission.

As discussed above, the high data rate, high throughput system requires an improved image transmission system to provide a responsive, scalable and cost effective transmission method. Referring to FIG. 6, a collection of X-ray systems 605, each capable of generating high volumes of data where each data set comprises a three-dimensional image of an object, is shown. Each X-ray system 605 is provided with a high speed dedicated network link which can take this three-dimensional data set directly to a high capacity storage array 645 at full bandwidth with little latency.

The database on the storage array 645 is managed by a system server 655 which is connected to the X-ray systems 605 and to the disk controller 665 via a network. A series of operators view three-dimensional image data at a series of networked workstations 635.

A job dispatcher application executes on the system server 655 and recognizes when new three-dimensional data is available. The job dispatcher application allocates a particular operator to review the new three-dimensional data set and the operator reports his or her findings back to the system server 655 via the network. At this point, the three-dimensional data set may be discarded, or it may be archived for medium term or long term storage.

Such a system can be very slow and use very large amounts of network bandwidth due to the size of the three-dimensional data sets. In the present invention, a 3D engine component 615 is coupled to the system, one 3D engine 615 per X-ray system 605. The 3D engine 615 processes the full three-dimensional data set that is generated by the X-ray system 605 in real time since it is directly connected to the X-Ray system 605 rather than being constrained by the bandwidth and latency of an intermediate network.

Figure 7:
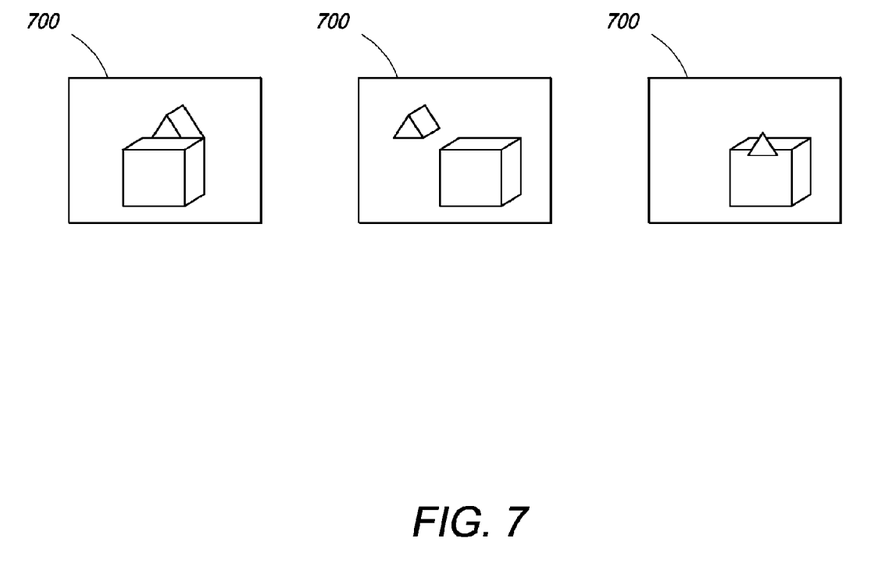
FIG. 7 depicts exemplary two-dimensional images derived from a full three-dimensional data set.

The 3D engine 615 processes the X-ray system 605 data into one or more two-dimensional images which represent projections through the three-dimensional data. Example two-dimensional images 700 that are derived from a full three-dimensional data set are provided in FIG. 7. The images 700 depict a three-dimensional triangular object and a cube like object in various orientations. It shall be evident to one skilled in the art that the size of the two-dimensional image is small compared to that of the full three-dimensional data set. Therefore, the network transmission time for the 2D image is short compared to that for the full 3D data set.

In the present invention, the 3D engine 615 output connects directly to the network such that the job dispatcher application running on the system server 655 can first dispatch a set of compact 2D images to an operator workstation 635 for immediate review. As a minimum, one 2D image will be rapidly generated and dispatched to the operator. More typically, 5 to 8 2D images will be pre-rendered and dispatched to an operator workstation 635. Very frequently, the operator can inspect the object with sufficient integrity that they do not need access to the full three-dimensional data set, thereby permitting the operator workstation 635 to be of a relatively low specification and reducing its cost compared to a full 3D workstation. The network can be almost any commercially available network of moderate bandwidth, such as a gigabit ethernet network.

In the event that the inspector can not inspect the object using 2D images only, the operator can signal to the job dispatcher that inspection is incomplete and that the image data should be transferred to a fully 3D operator workstation with a suitably trained operator for further review.

In this case, the job dispatcher will locate a suitably qualified 3D operator and will first send the set of 2D images to the operator for review. At this point, the operator will start to analyze the image data from 2D images only. In the background, the job dispatcher will start to transfer the full 3D data set to the 3D operator. Once the 3D data set has arrived at the operator workstation, the 3D engine inside the operator workstation will prepare the data set for 3D review by the operator. When the 3D data set is ready for viewing, the image workstation enables a set of three-dimensional image analysis tools and the operator can start to make use of these in an interactive fashion. The operator thus transfers from a 2D inspection mode to a 3D inspection mode as the necessary data becomes available.

Such a two-stage image transmission approach minimizes the time taken for the operator to start work but still provides all the data for review when needed. This is achieved using networks of modest bandwidth and latency with a consequently low cost.

In another embodiment, a network of operators, all of whom are qualified to inspect 3D data and all of whom have access to a 3D operator workstation, is provided. In this case, the operator will receive 2D data immediately, and can request full 3D image data when he or she is unable to complete his or her inspection using 2D pre-rendered images only. Again this allows a high reliability low cost network to be utilized while maintaining high inspection throughput.

While the exemplary embodiments of the present invention are described and illustrated herein, it will be appreciated that they are merely illustrative. It will be understood by those skilled in the art that various changes in form and detail may be made therein without departing from or offending the spirit and scope of the appended claims.

We claim:

1. An X-ray system comprising:
   a plurality of detectors for detecting and generating X-ray data;
   a scan controller coupled to the plurality of detectors, wherein the scan controller is configured to identify from the X-ray data, regions having required information and regions not having required information;
   a scan engine coupled to the plurality of detectors and the scan controller, wherein the scan engine receives the X-ray data and calibrates the X-ray data, based on regions identified by the scan controller that comprise required information; and
   an image reconstruction engine coupled to the scan engine and the scan controller, wherein the image reconstruction engine converts the calibrated X-ray data into one or more processed X-ray images.

2. The X-ray system of claim 1 further comprising a user input wherein the user input receives control information from a user and wherein the scan controller uses the control information to dynamically modulate processing of at least one of the X-ray data by the scan engine and of the calibrated X-ray data by the image reconstruction engine.

3. The X-ray system of claim 1 wherein the X-ray data is transmission data.

4. The X-ray system of claim 1 wherein the X-ray data is backscatter data.

5. The X-ray system of claim 1 further comprising a data visualization engine coupled to the image reconstruction engine for rendering the processed X-ray images to a human readable screen.

6. The X-ray system of claim 1 further comprising one or more storage devices coupled to one or more of the plurality of detectors, the scan engine, and the image reconstruction engine for storing data obtained from the plurality of detectors, the scan engine, and the image reconstruction engine.

7. The X-ray system of claim 1 wherein the scan controller issues instructions to the image reconstruction engine to process calibrated X-ray data from detectors corresponding to the regions comprising required information.

8. The X-ray system of claim 7 further comprising a data visualization engine wherein the data visualization engine receives from the image reconstruction engine a plurality of coordinates corresponding to the regions comprising required information.

9. The X-ray system of claim 1 wherein the scan controller issues instructions to the scan engine to modify a spatial resolution of a scan based upon the X-ray data.

10. The X-ray system of claim 9 wherein the spatial resolution is modified by generating a first spatial resolution in a scan direction and a second spatial resolution in a scan plane, the first spatial resolution being different than the second spatial resolution.

11. The X-ray system of claim 1 wherein the scan controller issues instructions to the scan engine to generate a first resolution and a second resolution in a scan, wherein the first resolution and the second resolution are different.

12. The X-ray system of claim 11 wherein the scan engine transmits the scan having the first resolution and the second resolution to the image reconstruction engine.

13. The X-ray system of claim 12 wherein the image reconstruction engine generates image data having variable resolution based on the scan having the first resolution and the second resolution.

14. The X-ray system of claim 12 wherein the image reconstruction engine generates image data having at least one of: an area of coarse pixelation, an area of medium granularity pixelation, and an area of high granularity pixelation.

15. A method for processing X-ray data, comprising:
   identifying, from the X-ray data, regions having required information and regions not having required information;
   calibrating the X-ray data based only on regions having the identified information and not on the regions not having required information;
   processing the calibrated X-ray data into one or more processed X-ray images; and
   issuing instructions to a scan engine to modify a spatial resolution of a scan based upon the X-ray data, wherein the spatial resolution is modified by generating a first spatial resolution in a scan direction and a second spatial resolution in a scan plane, the first spatial resolution being different than the second spatial resolution.

16. The method of claim 15 further comprising dynamically modulating processing of at least one of the X-ray data by a scan engine and of the calibrated X-ray data by an image reconstruction engine based on user inputted control information.

17. The method of claim 15 further comprising issuing instructions to an image reconstruction engine to process calibrated X-ray data from detectors corresponding to the regions having required information.

18. The method of claim 15 further comprising causing the scan engine to transmit the scan having the first resolution and the second resolution to an image reconstruction engine.

19. The method of claim 18 wherein the image reconstruction engine generates image data having variable resolution based on the scan having the first resolution and the second resolution.

20. The method of claim 18 wherein the image reconstruction engine generates image data having at least one of an area of coarse pixelation, an area of medium granularity pixelation, or an area of high granularity pixelation.

* * * * *